US012685610B2

(12) United States Patent
Gallant et al.

(10) Patent No.: US 12,685,610 B2
(45) Date of Patent: Jul. 21, 2026

(54) ADHESIVE SURGICAL REFERENCE MARKER UNIT

(71) Applicant: Medivis, Inc., New York, NY (US)

(72) Inventors: Jesse Harrison Gallant, New York, NY (US); Christopher Morley, New York, NY (US); Osamah Choudhry, New York, NY (US); Long Qian, Brooklyn, NY (US)

(73) Assignee: Medivis, Inc., New York, NY (US)

( * ) Notice: Subject to any disclaimer, the term of this patent is extended or adjusted under 35 U.S.C. 154(b) by 76 days.

(21) Appl. No.: 18/244,338

(22) Filed: Sep. 11, 2023

(65) Prior Publication Data

US 2025/0082429 A1     Mar. 13, 2025

(51) Int. Cl.
*A61B 90/00* (2016.01)

(52) U.S. Cl.
CPC ............. *A61B 90/39* (2016.02); *A61B 90/37* (2016.02); *A61B 2090/365* (2016.02); *A61B 2090/3937* (2016.02)

(58) Field of Classification Search
CPC ... A61B 90/39; A61B 90/37; A61B 2090/365; A61B 2090/3937; A61B 2090/372; A61B 2090/3983; A61B 2034/207
See application file for complete search history.

(56) References Cited

U.S. PATENT DOCUMENTS

| | | | | |
|---|---|---|---|---|
| 6,327,491 | B1 * | 12/2001 | Franklin | A61B 34/20 |
| | | | | 600/429 |
| 12,053,247 | B1 * | 8/2024 | Chiou | G06F 3/011 |
| 2009/0177077 | A1 * | 7/2009 | Piferi | G01R 33/3415 |
| | | | | 600/414 |
| 2010/0063388 | A1 * | 3/2010 | Solar | A61B 90/39 |
| | | | | 600/426 |
| 2014/0276959 | A1 * | 9/2014 | Oostman | A61F 2/10 |
| | | | | 606/133 |
| 2021/0169586 | A1 * | 6/2021 | Van Kampen | A61B 90/11 |
| 2023/0102358 | A1 * | 3/2023 | Shelton, IV | G06V 10/143 |
| | | | | 600/426 |

* cited by examiner

*Primary Examiner* — Brooke Labranche
(74) *Attorney, Agent, or Firm* — Cognition IP, P.C.; Edward Steakley; Justin White

(57) ABSTRACT

A surgical fiducial marker unit can include a main body, fiducial marker sites, and adhesive layer. The main body can have top and bottom surfaces, length, width, and thickness that is substantially less than the length and width. The fiducial marker sites can host surgical fiducial markers suitable for use with a separate augmented reality system and can be distributed across the main body top surface at fixed positions relative to each other to form a fixed positional arrangement that is asymmetrical. The adhesive layer can be disposed on the bottom surface of the main body and can securely adhere the main body to a patient during a surgical procedure. The surgical fiducial marker unit can include the surgical fiducial markers, each of which can define a circular disk having a flat upper surface. Each fiducial marker site can include a socket that receives a circular disk fiducial marker therein.

19 Claims, 6 Drawing Sheets

ADHESIVE SURGICAL REFERENCE MARKER UNIT

CROSS-REFERENCE TO RELATED APPLICATION

This application is related to commonly owned U.S. patent application Ser. No. 18/244,335 filed on Sep. 11, 2023 and titled "SURGICAL CATHETER SNAP TOOL," which application is hereby incorporated herein by reference in its entirety.

TECHNICAL FIELD

The present disclosure relates generally to medical devices, and more particularly to surgical tools and devices used during medical procedures.

BACKGROUND

Planning and navigation are necessary for many medical procedures, such as live surgeries and also practice, training, planning, and developmental procedures. Surgical teams typically have a plan based on medical imagery before ever entering an operating room. Conventional medical imaging systems such as X-ray, MRI, CT, and others have limitations regarding two-dimensional and three-dimensional images, however, and surgeons often need to consider numerous image views and slices to plan surgical procedures. Recent medical advances leverage these applications of medical imagery and surgical plans by using a computer-aided augmented reality environment, which can allow for the tracking of patients and physical instruments during surgical procedures by using fiducial markers and tracking components.

Unfortunately, conventional tracking systems are often limited in their ability to accurately generate, render, and apply virtual interactions in an augmented reality environment based on the orientations and positions of physical instruments with respect to those of physical landmarks identified on a patient body, particularly when things move during surgery. Unstable or unreliable positioning of fiducial markers can play a role in these issues. Limited or inaccurate tracking can then affect the overall performance of such systems during surgical procedures, and the need for accuracy in this regard can lead to overly cumbersome or complex attachment devices and systems.

While traditional ways of virtually tracking items during surgery have worked well in the past, improvements are always helpful. In particular, what is desired are medical systems and devices that facilitate the stable and reliable positioning of fiducial markers during surgery in a simple and streamlined manner.

SUMMARY

It is an advantage of the present disclosure to provide medical systems and devices that facilitate the stable and reliable positioning of fiducial markers during surgery in a simple and streamlined manner. Various embodiments disclosed herein relate to features, apparatuses, systems, and methods of use for surgical tools configured for use with augmented reality systems. This can involve surgical reference marker units configured for the positioning of fiducial markers during augmented reality aided surgery.

In various embodiments of the present disclosure, a surgical fiducial marker unit can include a main body, a plurality of fiducial marker sites, and an adhesive layer. The main body can have a top surface, a bottom surface, a length, a width, and a thickness that is substantially less than both the length and the width. The plurality of fiducial marker sites can be coupled to the main body and can be configured to host a plurality of surgical fiducial markers suitable for use with a separate augmented reality system. The plurality of fiducial marker sites can be distributed across the top surface of the main body at fixed positions relative to each other to form a fixed positional arrangement that is asymmetrical. The adhesive layer can be disposed on the bottom surface of the main body and can be configured to securely adhere the main body to a patient during a surgical procedure.

In various detailed embodiments, the surgical fiducial marker unit can also include the plurality of surgical fiducial markers themselves, each of which can be coupled to a respective fiducial marker site. Each of the plurality of surgical fiducial markers can define a circular disk having a flat upper surface configured to be visible by a component of the separate augmented reality system when the circular disk is coupled to one of the fiducial marker sites. In some arrangements, each circular disk can include a thin film across its upper surface that is configured to be detected by the component of the separate augmented reality system. Each of the plurality of fiducial marker sites can include a socket having a size and shape that corresponds to the size and shape of an entire circular disk that forms a surgical fiducial marker. Such a socket can be configured to receive a respective entire circular disk therein. Each socket can be oriented at an angle with respect to the top surface of the main body such that the flat upper surface of an entire circular disk received therein faces a different direction than the direction faced by the top surface of the main body. In some arrangements, all sockets at all fiducial marker sites can be oriented at the same angle with respect to the main body top surface.

In further detailed embodiments, the main body can include a central region that has at least some of the plurality of fiducial marker sites and also multiple extensions from the central region that collectively have at least some of the plurality of fiducial marker sites. The main body can define a curved shape that conforms to the curved shape of a patient forehead. In some arrangements, the main body can be formed from a rigid material configured to maintain the fixed positions of the plurality of fiducial marker sites. In some embodiments, the main body can be formed from a flexible material configured to facilitate greater conformity between the main body and the patient when the main body is securely adhered to the patient. The plurality of fiducial marker sites can include at least four sites, which can be exactly seven sites in some configurations. In various embodiments, the surgical fiducial marker unit can also include an augmented reality system reference feature located on the top surface of the main body, and this augmented reality system reference feature can be separate from the reference marker sites. This augmented reality system reference feature can include a divot extending into the top surface of the main body, and the divot can be configured as a known reference point for registering a point of a separate handheld localizer device.

In various further embodiments of the present disclosure, a fiducial device configured for use with a surgical augmented reality system can include a surgical fiducial marker and a socket. The surgical fiducial marker can define a circular disk having a flat upper surface configured to be detected by a detection component of the surgical augmented reality system. The socket can have a size and shape that corresponds to the surgical fiducial marker and that holds the entire surgical fiducial marker therein. The socket can be configured to be coupled to a separate surgical fiducial marker unit having multiple fiducial marker sites.

In various detailed embodiments, the fiducial device can also include a thin film located across the flat upper surface of the circular disk. This thin film can be configured to be the item detected by the detection component. Also, the socket can be further configured to be oriented at an angle with respect to a surface of the separate surgical fiducial marker unit. This angle of orientation can be adjustable in some arrangements. In some embodiments, the socket can be configured to be able to coordinate with other similar sockets such that the fiducial device is configured to be part of an array of coordinated fiducial devices on the separate surgical fiducial marker unit.

Other apparatuses, methods, features, and advantages of the disclosure will be or will become apparent to one with skill in the art upon examination of the following figures and detailed description. It is intended that all such additional apparatuses, methods, features and advantages be included within this description, be within the scope of the disclosure, and be protected by the accompanying claims.

BRIEF DESCRIPTION OF THE DRAWINGS

The included drawings are for illustrative purposes and serve only to provide examples of possible structures, arrangements, and methods of use for adhesive surgical reference marker units and related system components. These drawings in no way limit any changes in form and detail that may be made to the disclosure by one skilled in the art without departing from the spirit and scope of the disclosure.

DETAILED DESCRIPTION

Exemplary applications of apparatuses, systems, and methods according to the present disclosure are described in this section. These examples are being provided solely to add context and aid in the understanding of the disclosure. It will thus be apparent to one skilled in the art that the present disclosure may be practiced without some or all of these specific details provided herein. In some instances, well known process steps have not been described in detail in order to avoid unnecessarily obscuring the present disclosure. Other applications are possible, such that the following examples should not be taken as limiting. In the following detailed description, references are made to the accompanying drawings, which form a part of the description and in which are shown, by way of illustration, specific embodiments of the present disclosure. Although these embodiments are described in sufficient detail to enable one skilled in the art to practice the disclosure, it is understood that these examples are not limiting, such that other embodiments may be used, and changes may be made without departing from the spirit and scope of the disclosure.

The present disclosure relates in various embodiments to features, apparatuses, systems, and methods of use for surgical tools and devices configured for use with augmented reality systems. Such tools and devices can facilitate the stable and reliable positioning of surgical fiducial markers during a surgery or other medical procedure. This can involve surgical fiducial marker units that can host and reliably arrange multiple surgical fiducial markers with respect to another object, such as a patient. Such reference marker or fiducial marker units can generally include a main body having fiducial marker sites and/or surgical fiducial markers distributed across a top surface and an adhesive layer disposed on a bottom surface. This can also involve specific fiducial devices that include a surgical fiducial marker defining a circular disk having a flat upper surface and a socket configured to hold the entire disk therein.

Although various embodiments disclosed herein discuss specific surgical fiducial marker units configured to adhere to a patient, it will be readily appreciated that such units can alternatively be adhered or coupled to other objects as well. It will also be understood that at least some of the disclosed embodiments can be used in other augmented reality applications beyond surgical applications. Other applications, uses, arrangements, and extrapolations beyond the illustrated embodiments are also contemplated.

Figure 1:
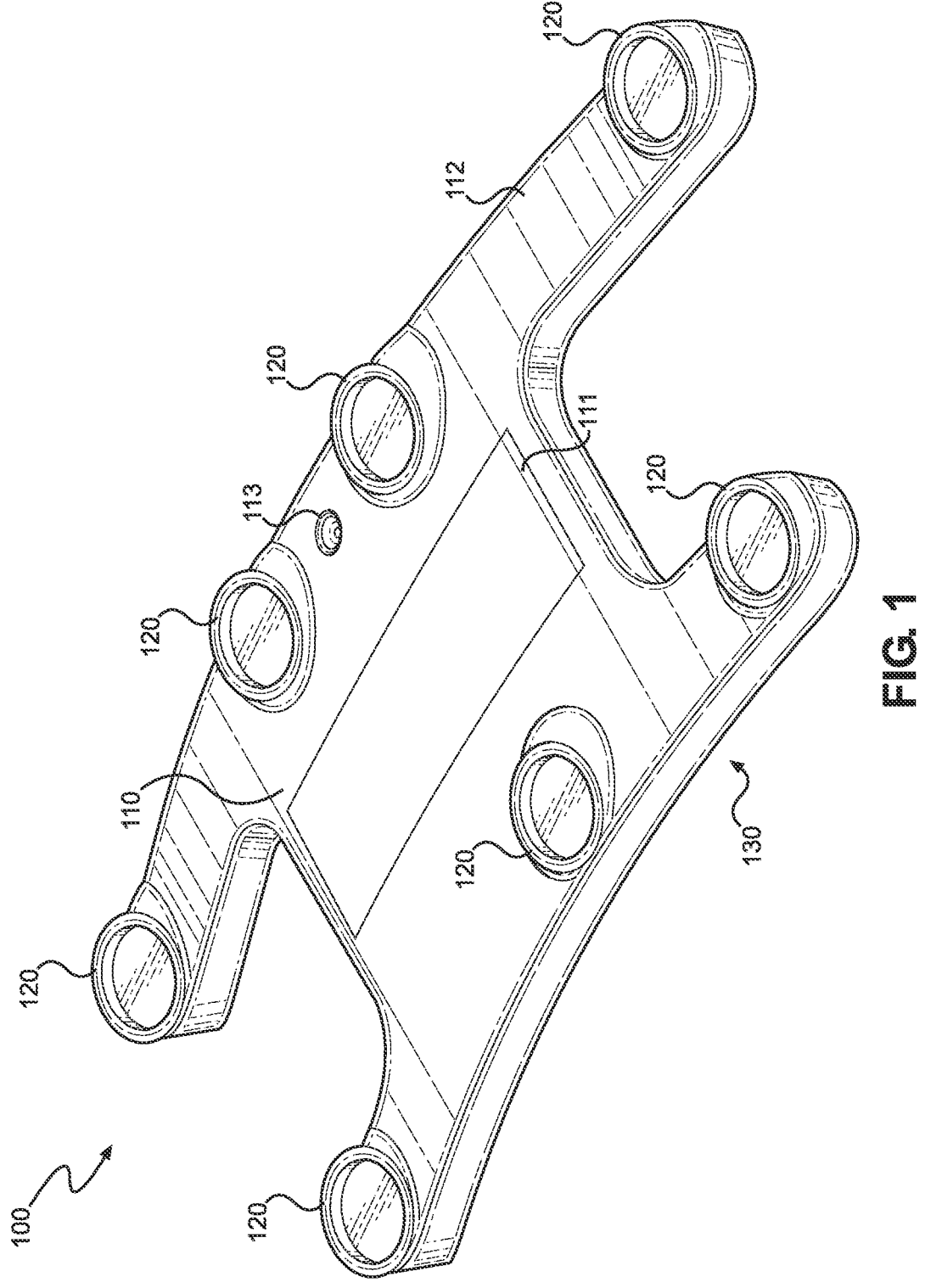
FIG. 1 illustrates in top perspective view an example surgical fiducial marker unit according to one embodiment of the present disclosure.

Referring first to FIG. 1, an example surgical fiducial marker unit is illustrated in top perspective view. Surgical fiducial marker unit 100, which can alternatively be called an adhesive surgical reference marker unit, can include a main body 110, a plurality of fiducial marker sites 120, and an adhesive layer 130. As shown, main body 110 can have a top surface, a bottom surface, a length, a width, and a thickness that is substantially less than both the length and the width. Main body 110 can include a central region 111 that has at least some of the fiducial marker sites 120 and multiple extensions 112 from the central region that collectively have at least some of the fiducial marker sites. As shown, main body 110 can define a curved shape that can conform to a curved shape, such as to a patient forehead or other curved object. Also, main body 110 can be formed from a rigid material configured to maintain the fixed positions of fiducial marker sites 120.

The plurality of fiducial marker sites 120 can be coupled to main body 110 and can be configured to host a plurality of surgical fiducial markers suitable for use with a separate augmented reality system. Fiducial marker sites 120 can be distributed across the top surface of main body 110 at fixed positions relative to each other to form a fixed positional arrangement that is asymmetrical, as shown. Although seven fiducial marker sites 120 are shown in FIG. 1 and other embodiments disclosed herein, it will be readily appreciated that more or fewer fiducial marker sites can be used for a given surgical fiducial marker unit. For example, at least four fiducial marker sites can be used in some arrangements.

Adhesive layer 130 can be disposed on the bottom surface of main body 130, and this adhesive layer can be configured to securely adhere the main body to a patient during a surgical procedure. Alternatively, adhesive layer 130 can securely adhere the main body to any other suitable object during a process involving an augmented reality system. Adhesive layer can be, for example, a double sided adhesive pad, tape, or other item that can adhere on one side to the bottom surface of main body 130 and on an opposite side to a patient or other object.

In some arrangements, an augmented reality system reference feature 113 can be located on the top surface of main body 110, and this feature can be separate from fiducial marker sites 120. Augmented reality system reference feature 113 can include a divot extending into the top surface of main body 110, and this divot can be configured as a known reference item for registering a point of a separate handheld localizer device. For example, divot 113 can be configured to accept a pointed nose or other tip of a separate surgical catheter snap tool for referencing locations within an augmented reality environment. Further details regarding such a device can be found in commonly owned U.S. patent application Ser. No. 18/244,335 filed on Sep. 10, 2023 and titled "SURGICAL CATHETER SNAP TOOL," which application is again hereby incorporated herein by reference in its entirety.

Figure 2A:
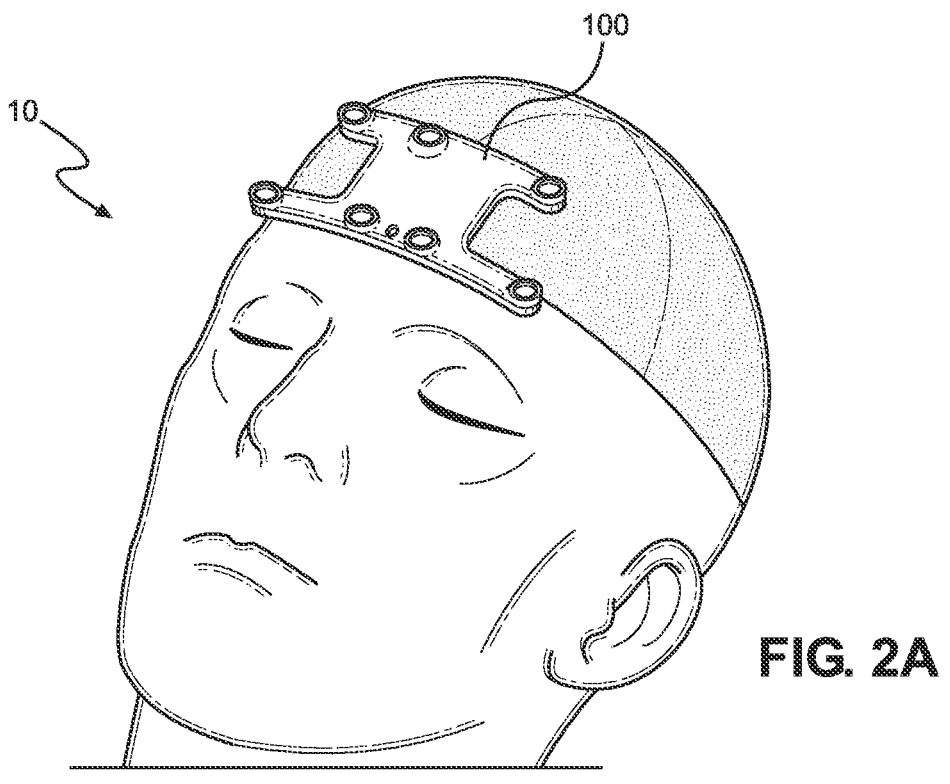
FIG. 2A illustrates in front perspective view an example surgical fiducial marker unit adhered to the forehead of a patient according to one embodiment of the present disclosure.
Figure 2B:
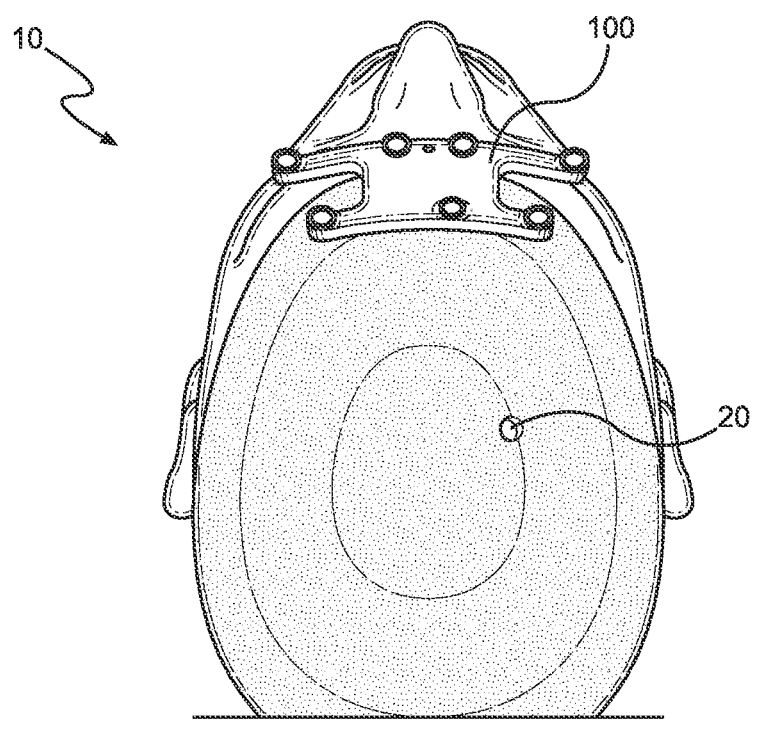
FIG. 2B illustrates in top plan view an example surgical fiducial marker unit adhered to the forehead of a patient according to one embodiment of the present disclosure.

FIGS. 2A and 2B depict an example surgical fiducial marker unit adhered to the forehead of a patient in front perspective and top plan views respectively. In various embodiments, surgical fiducial marker unit 100 can be used during an external ventricular drainage ("EVD") procedure, such as during brain surgery. For such a procedure, surgical fiducial marker unit 100 can be adhered to the forehead of a patient 10 and can alternatively be called a forehead reference marker unit or device.

In some arrangements, an opening 20 or other surgical site on the head of patient 10 can be arranged for an EVD procedure, which can involve use of the separate surgical catheter snap tool noted above. Interactions between this catheter snap tool, surgical fiducial marker unit 100, the surgeon, and various other components can provide for an accurate augmented reality environment that includes the head of patient 10, even when the patient changes position or moves. Such interactions can include, for example, registering a tip or pointed nose of the catheter snap tool at reference feature 113 on surgical fiducial marker unit 100, as well as system detections of fiducial markers on the catheter snap tool, the surgical fiducial marker unit, or both.

Figure 3A:
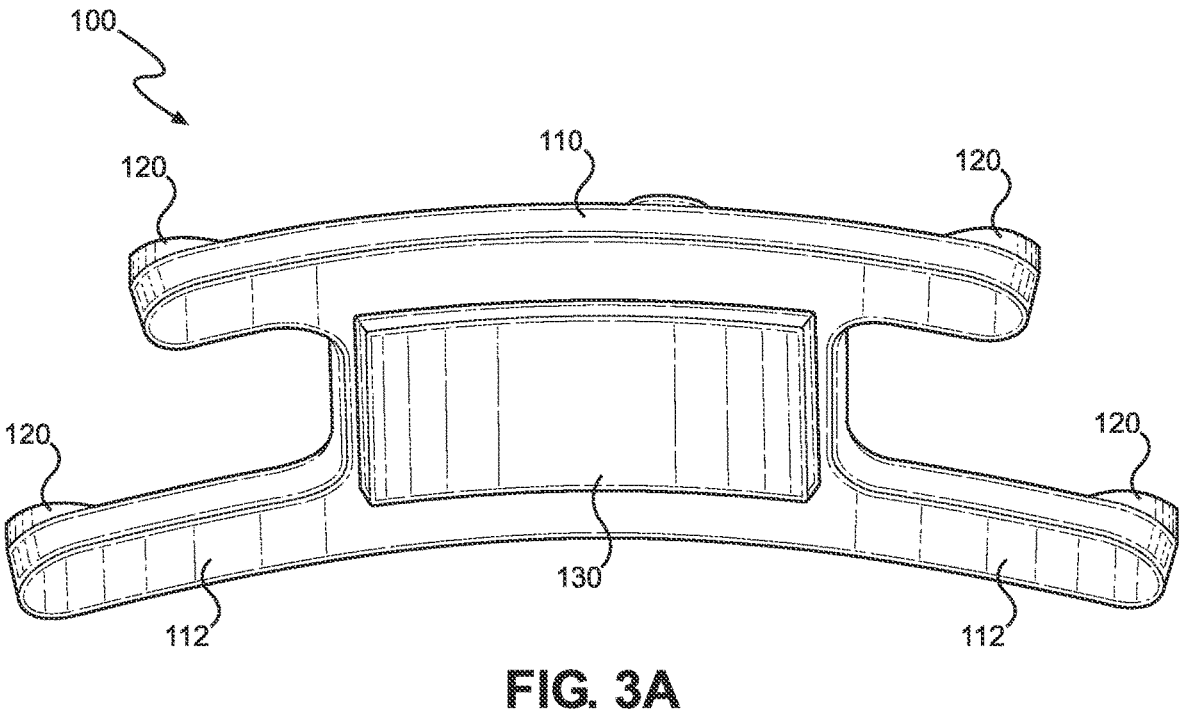
FIG. 3A illustrates in bottom perspective view the surgical fiducial marker unit of FIG. 1 according to one embodiment of the present disclosure.
Figure 3B:
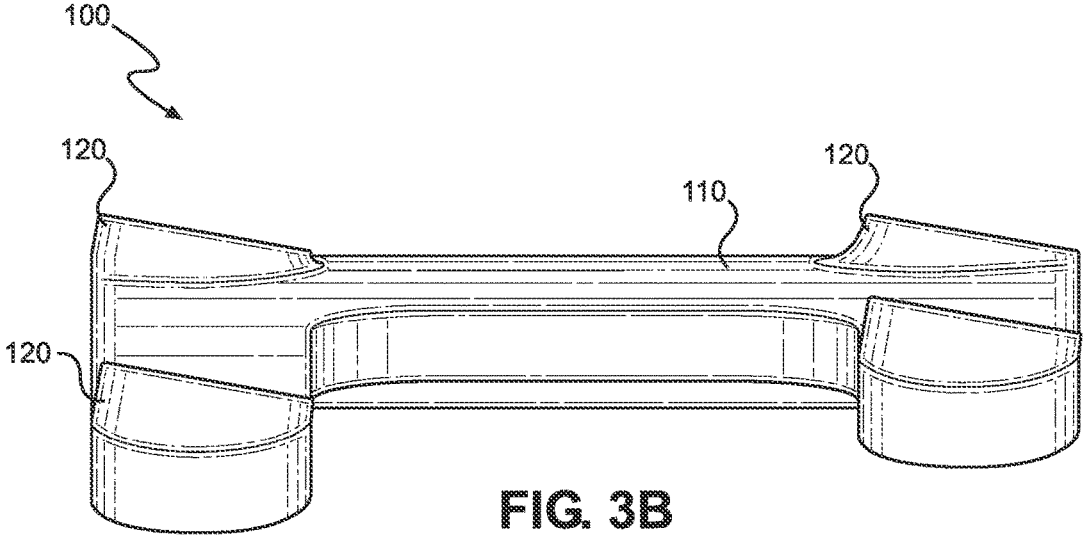
FIG. 3B illustrates in side elevation view the surgical fiducial marker unit of FIG. 1 according to one embodiment of the present disclosure.

Continuing with FIGS. 3A and 3B, the surgical fiducial marker unit of FIG. 1 is shown in bottom perspective and side elevation views respectively. These views provide other perspectives for surgical fiducial marker unit 100 and its various components and features, such as main body 110, fiducial marker sites 120, adhesive layer 130, and extensions 112. As can be seen in FIG. 3B, one or more fiducial marker sites 120 can be oriented at an angle with respect to the top surface of main body 110, such that they face a different direction than the direction faced by the top surface of the main body. In some arrangements, all fiducial marker sites 120 can be oriented at the same offset angle with respect to the top surface of main body 110. This angle can be about 15 degrees, for example, although greater or smaller angles are possible.

This offset angle orientation can facilitate better visibility and access to fiducial markers having flat upper surfaces that are installed within fiducial marker sites 120. In some arrangements, surgical fiducial marker used with unit 100 can define a circular disk shape having flat upper and lower surfaces, and each fiducial marker site 120 can define or include a socket configured to hold such a circular disk firmly therein.

Figures 4A, 4B:
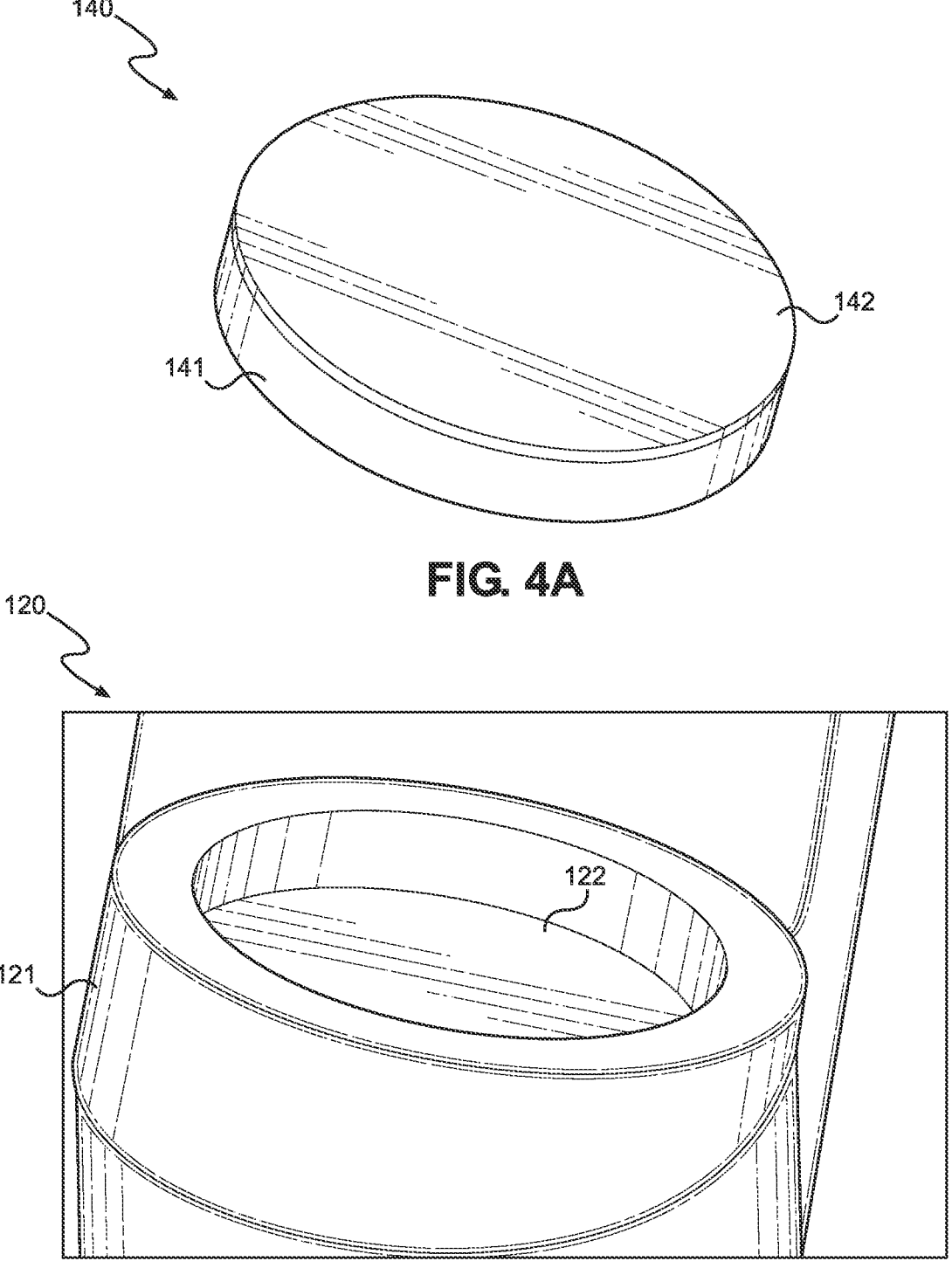
FIG. 4A illustrates in side perspective view an example disk shaped surgical fiducial marker according to one embodiment of the present disclosure.
FIG. 4B illustrates in side perspective view an example socket shaped fiducial marker site according to one embodiment of the present disclosure.

FIG. 4A illustrates in side perspective view an example disk shaped surgical fiducial marker, while FIG. 4B illustrates in side perspective view an example socket shaped fiducial marker site. Disk shaped surgical fiducial marker 140 can include a disk shaped body 141 having a flat upper surface and a flat lower surface, as well as a thin circular film 142 or other layer or item covering the top surface of the body. Circular film 142 can feature one or more components that can function as infrared reflective items, such that cameras, detectors, or other augmented system reality devices can detect the circular film and overall disk shaped surgical fiducial marker 140. Alternatively, the body 141 of disk shaped surgical fiducial marker 140 can be formed from an infrared reflective material such that circular film 142 is not necessary.

Disk shaped surgical fiducial marker 140 can be configured to be installed within fiducial marker site 120, which can include or take the shape of a socket. As such, fiducial marker site 120 can include a socket wall 121 that encircles a recess 122 formed therein. In various arrangements, disk shaped surgical fiducial marker 140 and socket shaped fiducial marker site 120 can both be sized and shaped to mate with each other such that the fiducial marker fits firmly within the socket and such that the upper surface lays flush or nearly flush with the top edge of socket wall 121. Surgical fiducial marker 140 can be snapped or press-fit into the socket, and can be permanently affixed therein, such as by glue or other adhesive.

While the foregoing reflective disks have been illustrated and described herein as a particular illustrative example for the surgical fiducial markers to be used with a surgical fiducial marker unit, it will be understood that other forms, shapes, and types of fiducial markers can also or alternatively be used. For example, other suitable fiducial markers can include reflective spheres, cubes, prisms, lines, dots, or other alternative shapes. Similarly, fiducial marker sites used for such alternative arrangements can also vary to conform to the type and shape of any such alternative fiducial markers. For example, a cube shaped socket could be used for a cube shaped fiducial marker. Other variations and arrangements are also possible.

Figures 5A, 5B:
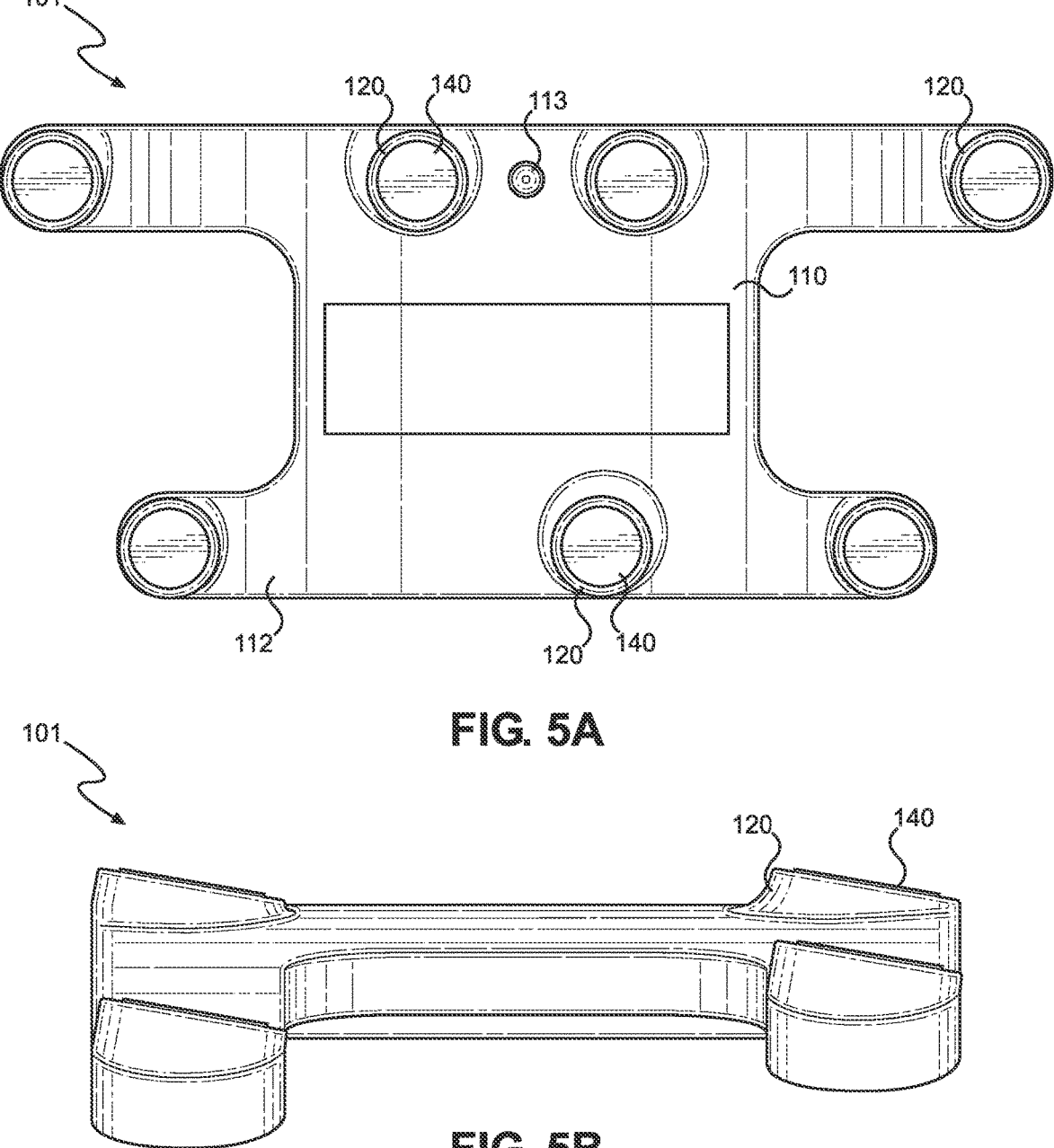
FIG. 5A illustrates in top plan view an example surgical fiducial marker unit with disk shaped surgical fiducial markers according to one embodiment of the present disclosure.
FIG. 5B illustrates in side elevation view the surgical fiducial marker unit of FIG. 5A according to one embodiment of the present disclosure.

FIGS. 5A and 5B illustrate an example surgical fiducial marker unit with disk shaped surgical fiducial markers in top plan and side elevation views respectively. Surgical fiducial marker unit 101 can be identical to unit 100 above, only with disk shaped surgical fiducial markers 140 installed thereto. As shown, each disk shaped surgical fiducial marker 140 can be firmly and snugly installed into a respective socket shaped fiducial marker site 120. As noted above, fiducial marker sites 120 can be oriented at an angle with respect to the top surface of main body 110. Accordingly, the flat upper surfaces of each disk shaped surgical fiducial marker 140 can also face in the same angled orientation.

Socket shaped fiducial marker sites 120 can be coupled to main body 110 or can alternatively be integrally formed with the main body. In some arrangements, one or more of the fiducial marker sites 120 can be configured to have its offset facing angle adjusted. In other arrangements, all of the fiducial marker sites 120 can be affixed at a permanent offset angle, and all can be oriented at the same angle. In various embodiments, the entire surgical fiducial marker unit 100 can be designed as a single use disposable item.

Figure 6:
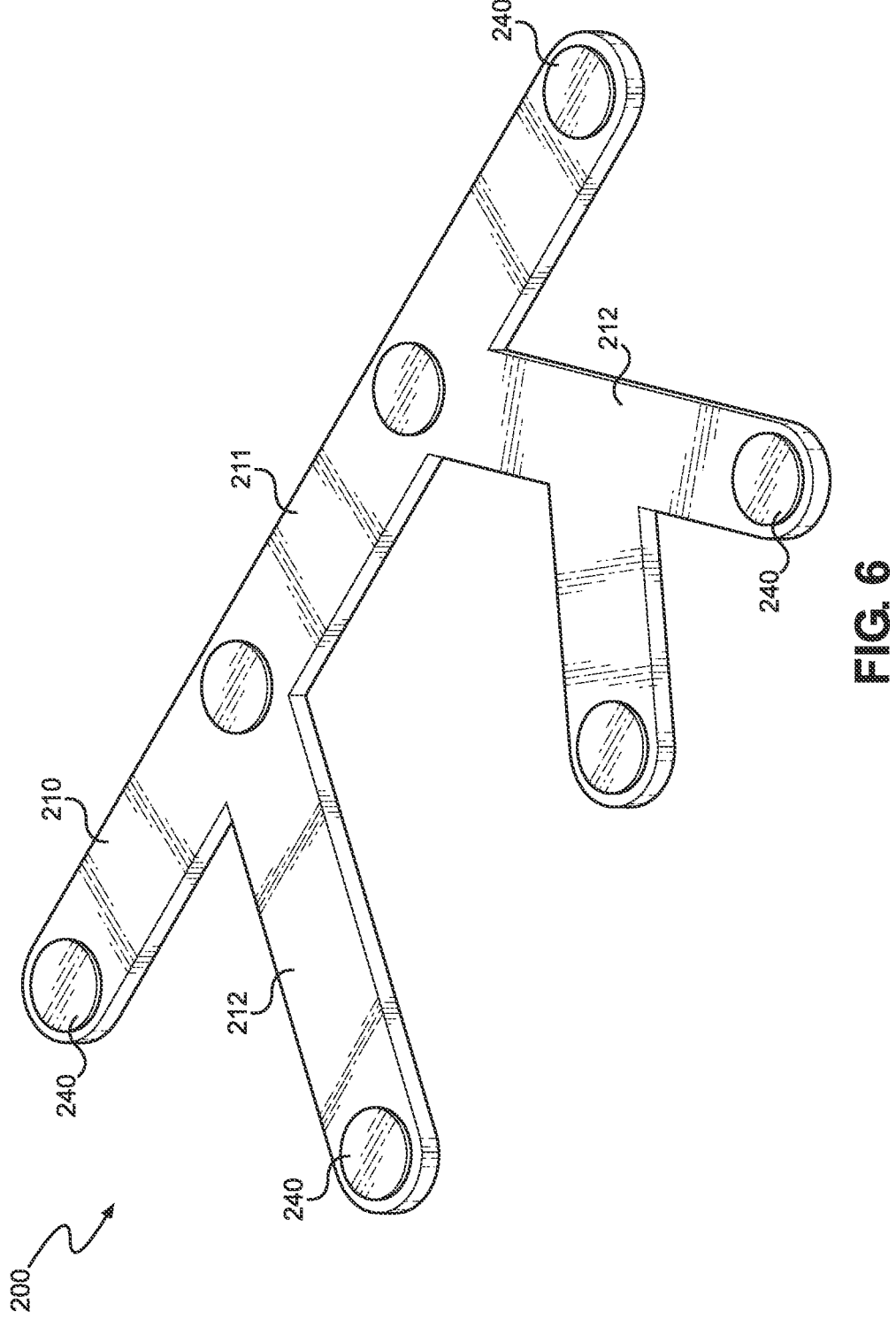
FIG. 6 illustrates in top perspective view an example alternative surgical fiducial marker unit according to one embodiment of the present disclosure.

Lastly, FIG. 6 illustrates in top perspective view an example alternative surgical fiducial marker unit according to an alternative embodiment of the present disclosure. Surgical fiducial marker unit 200 can include a main body 210 and a plurality of surgical fiducial markers 240 coupled to the top surface of the main body. Main body 210 can include a central region 211 and multiple extensions 212 extending from the central region. Each of central region 211 and extensions 212 can include one or more surgical fiducial markers 240, and all of these fiducial markers can be arranged in a pattern that is asymmetrical.

Main body 210 can be formed from a flexible foam material that is generally sticky in nature, such that the bottom surface of the main body can be adhered to a patient or other suitable object of interest. This flexible foam material can be configured to facilitate greater conformity between main body 210 and the patient when the main body is securely adhered to the patient. The top surface of main body 210 can also be sufficiently sticky to facilitate adhering the surgical fiducial markers 240 thereto. Alternatively, or in addition, a tape, glue, or other adhesive material can be used to facilitate affixing fiducial markers 240 to main body 210.

In some arrangements, surgical fiducial markers 240 can also be disk shaped with a flat upper surface. These fiducial markers can be identical or substantially similar to disk shaped surgical fiducial markers 140 above. Alternatively, surgical fiducial markers 240 can be substantially thinner and can be formed from a more flexible material suitable for use with the flexible foam material of main body 210.

Although the foregoing disclosure has been described in detail by way of illustration and example for purposes of clarity and understanding, it will be recognized that the above described disclosure may be embodied in numerous other specific variations and embodiments without departing from the spirit or essential characteristics of the disclosure. Certain changes and modifications may be practiced, and it is understood that the disclosure is not to be limited by the foregoing details, but rather is to be defined by the scope of the appended claims.

What is claimed is:

1. A surgical fiducial marker unit, comprising:
   a main body having a solid central region, a top surface, a bottom surface, a length, a width, and a thickness, wherein the thickness is substantially less than both the length and the width and is substantially the same across the entire main body;
   a plurality of fiducial marker sites coupled to the main body and configured to host a plurality of surgical fiducial markers suitable for use with a separate augmented reality system, each of the plurality of fiducial marker sites including a socket having a size and shape that corresponds to the size and shape of an entire surgical fiducial marker and that is configured to receive the entire surgical fiducial marker therein, each socket having a socket wall that surrounds a recess and an open top such that an upper surface of the surgical fiducial marker fitted within the recess is optically visible, wherein the plurality of fiducial marker sites are distributed across the top surface at fixed positions relative to each other to form a fixed positional arrangement that is asymmetrical; and
   an adhesive layer disposed on the bottom surface of the solid central region, wherein the adhesive layer is configured to securely adhere the main body to a patient during a surgical procedure.

2. The surgical fiducial marker unit of claim 1, further comprising:
   the plurality of surgical fiducial markers coupled to the plurality of fiducial marker sites.

3. The surgical fiducial marker unit of claim 1, wherein each of the plurality of surgical fiducial markers defines a circular disk having a flat upper surface configured to be optically visible by a component of the separate augmented reality system when the circular disk is coupled to one of the fiducial marker sites.

4. The surgical fiducial marker unit of claim 3, wherein each socket is oriented at an angle with respect to the top surface of the main body such that the flat upper surface of an entire circular disk received therein faces a different direction than the direction faced by the top surface of the main body.

5. The surgical fiducial marker unit of claim 4, wherein all sockets at all fiducial marker sites are oriented at the same angle with respect to the top surface of the main body.

6. The surgical fiducial marker unit of claim 1, wherein the main body solid central region has at least some of the plurality of fiducial marker sites, and wherein the main body further includes multiple extensions from the solid central region that collectively have at least some of the plurality of fiducial marker sites at locations that are substantially removed from the solid central region.

7. The surgical fiducial marker unit of claim 1, wherein the main body defines a curved shape that conforms to a curved shape of the forehead of the patient.

8. The surgical fiducial marker unit of claim 1, wherein the main body is formed from a rigid material configured to maintain the fixed positions of the plurality of fiducial marker sites.

9. The surgical fiducial marker unit of claim 1, wherein the main body is formed from a flexible material configured to facilitate greater conformity between the main body and the patient when the main body is securely adhered to the patient.

10. The surgical fiducial marker unit of claim 1, wherein the plurality of fiducial marker sites includes at least four fiducial marker sites.

11. The surgical fiducial marker unit of claim 1, further comprising:
   an augmented reality system reference feature located on the top surface of the main body, wherein the augmented reality system reference feature is separate from the plurality of reference marker sites.

12. The surgical fiducial marker unit of claim 11, wherein the augmented reality system reference feature includes a divot extending into the top surface, the divot being configured as a known reference point for registering a point of a separate handheld localizer device.

13. The surgical fiducial marker unit of claim 1, wherein the main body further includes multiple extensions from the solid central region, each of the multiple extensions forming an arm shape that extends away from the solid central region in a lateral direction for a distance that is greater than the size of any of the fiducial marker sites.

14. The surgical fiducial marker unit of claim 13, wherein at least two of the arm shaped extensions extend away from the solid central region for a distance that is at least three times the size any of the fiducial marker sites.

15. The surgical fiducial marker unit of claim 13, wherein each of the multiple extensions includes a fiducial marker site situated at a distal end thereof.

16. A fiducial device configured for use with a surgical augmented reality system, the fiducial device comprising: a surgical fiducial marker defining a circular disk having a flat upper surface configured to be detected by a detection component of the surgical augmented reality system; and a socket having a size and shape that corresponds to the surgical fiducial marker and that holds the surgical fiducial marker therein, the socket having a socket wall that surrounds a recess and an open top such that the flat upper surface of the surgical fiducial marker fitted within the recess protrudes above the top edge of the socket wall and is optically visible, wherein the socket is coupled to a separate surgical fiducial marker unit having multiple fiducial marker sites, wherein the socket is further oriented at an angle with respect to a surface of the separate fiducial marker unit.

17. The fiducial device of claim 16, further comprising:
   a thin film located across the flat upper surface of the circular disk, wherein the thin film is configured to be detected by the detection component.

18. The fiducial device of claim 16, wherein the angle of orientation is adjustable.

19. The fiducial device of claim 16, wherein the socket is further configured to be able to coordinate with other similar sockets such that the fiducial device is configured to be part of an array of coordinated fiducial devices on the separate surgical fiducial marker unit.

\*  \*  \*  \*  \*